(12) United States Patent
Otto et al.

(10) Patent No.: US 8,862,218 B2
(45) Date of Patent: Oct. 14, 2014

(54) SCALP POTENTIAL MEASURING METHOD AND APPARATUS

(75) Inventors: Edward J. Otto, Kenmore East (AU); Daniel R. Bongers, Kenmore East (AU)

(73) Assignee: EdanSafe Pty. Ltd., Pinjarra Hills, Queensland (AU)

( * ) Notice: Subject to any disclaimer, the term of this patent is extended or adjusted under 35 U.S.C. 154(b) by 499 days.

(21) Appl. No.: 12/665,920

(22) PCT Filed: Jun. 23, 2008

(86) PCT No.: PCT/AU2008/000919
§ 371 (c)(1),
(2), (4) Date: Dec. 21, 2009

(87) PCT Pub. No.: WO2009/000030
PCT Pub. Date: Dec. 31, 2008

(65) Prior Publication Data
US 2010/0145217 A1    Jun. 10, 2010

(30) Foreign Application Priority Data

Jun. 22, 2007 (AU) ............................... 2007903384

(51) Int. Cl.
*A61B 5/04* (2006.01)
*A61B 5/00* (2006.01)
*A61B 5/0476* (2006.01)

(52) U.S. Cl.
CPC ............ *A61B 5/0476* (2013.01); *A61B 5/7225* (2013.01); *A61B 5/6814* (2013.01); *A61B 5/04004* (2013.01)
USPC ......................................... 600/544; 702/189

(58) Field of Classification Search
USPC .......................................... 600/544; 702/189
See application file for complete search history.

(56) References Cited

U.S. PATENT DOCUMENTS

| 3,577,074 | A | * | 5/1971 | Praglin ........................... 324/98 |
| 4,967,038 | A | | 10/1990 | Gevins et al. |
| 5,678,559 | A | | 10/1997 | Drakulic |
| 2004/0073129 | A1 | | 4/2004 | Caldwell et al. |
| 2006/0058694 | A1 | * | 3/2006 | Clark et al. .................... 600/509 |
| 2006/0167370 | A1 | * | 7/2006 | Greenwald et al. ........... 600/544 |
| 2008/0190203 | A1 | * | 8/2008 | Sugimori .................... 73/514.32 |

FOREIGN PATENT DOCUMENTS

| DE | 254138 A1 | 12/1986 | |
| WO | WO 2005/065544 | 4/2004 | |
| WO | WO 2005120339 A1 * | 12/2005 | ............... A61B 5/04 |

OTHER PUBLICATIONS

International Search Report for PCT/AU2008/000919 completed Jul. 25, 2008.

(Continued)

*Primary Examiner* — Navin Natnithithadha
*Assistant Examiner* — Etsub Berhanu
(74) *Attorney, Agent, or Firm* — Barnes & Thornburg LLP

(57) ABSTRACT

An apparatus for measuring scalp potential is disclosed, which comprises a plurality of sensors and a pre-amplifier coupled to these sensors. The sensors are adapted to measure a raw scalp potential measurement though a hair and air interface, and may be considered as a difference, reference or common measurement. The interface presents a high and variable source impedance coupling to the scalp. The pre-amplifier is adapted to have an input impedance significantly higher than that presented by the source interface, and receives the raw scalp potential measurement to produce a pre-amplified scalp potential measurement.

10 Claims, 11 Drawing Sheets

(56) References Cited

OTHER PUBLICATIONS

Wilh-Pieck-Univ Rostock, "EEG-VECP Miniature Pre-Amplifier Electrode has Impedance Converting Pre-Amplifer Included With Electrode That is Linked to Main EEG Amplifier by 4 Low Impedance Cable", Feb. 17, 1988, *Derwent Publications LTD.*, Accession No. 88-191046/28, Class P31, DD254138A.

Iguchi, H., "Wearable Electroencephalograph System With Preamplified Electrodes", Jul. 1994, *Medical & Biological Engineering & Computing*, vol. 32, No. 4, pp. 459-461.

* cited by examiner

SCALP POTENTIAL MEASURING METHOD AND APPARATUS

CROSS REFERENCE TO RELATED APPLICATIONS

This application is the U.S. national phase of PCT/AU2008/000919 filed Jun. 23, 2008. PCT/AU2008/000919 claims benefit under the Paris Convention to AU 2007903384 filed Jun. 22, 2007. The disclosures of both of AU 2007903384 and PCT/AU2008/000919 are hereby incorporated herein by reference.

FIELD OF THE INVENTION

The present disclosure relates generally to medial devices and in particular to medical devices for producing an electroencephalogram (EEG). However, it will be appreciated that the invention is not limited to this particular field of use.

The embodiments have been developed primarily as method and apparatus for measuring scalp potential and will be described hereinafter with reference to this application.

BACKGROUND OF THE INVENTION

Any discussion of the prior art throughout the specification should in no way be considered as an admission that such prior art is widely known or forms part of the common general knowledge in the field.

EEG waveforms are routinely recorded in clinical settings for the diagnosis of epilepsy and other conditions that are evident in brain wave data. These EEG waveforms are typically measured using an array of sensors applied to a headpiece secured to the head by a straps extending from the headpiece and fastened under the chin.

The application of these sensors typically requires parting the hair and the removal of any dead scalp tissue by applying a conductive abrasive gel. The sensors are coupled to the headpiece, typically though use of a clip or screw, such that when the headpiece is used, it applies a positive pressure to the sensor toward the scalp. This method of arranging the sensors typically allows continuous EEG measurement for about an hour before the scalp preparation must be reapplied.

An alternative solution, e.g. as proposed by Advanced Brain Monitoring Inc, provides a wireless sensor headset which can be worn for about eight hours of continuous use. However, for this device to provide a connection between the sensors and the scalp for eight hours, the sensor excretes a conductive cream through the hair during use. The current art typically teaches methods of improving and maintaining a stable conductive connection between the sensor and the scalp to overcome this problem.

There is a need in the art for a method and apparatus of measuring scalp potential that is less demanding on its requirement for conductivity to the scalp.

SUMMARY OF THE INVENTION

It is an object to provide an improved method or apparatus for measuring scalp potential that can be effectively used with relatively little or no scalp preparation.

According to a first aspect of the invention there is provided an apparatus for scalp potential measuring comprising:
  a plurality of sensors adapted to measure a raw scalp potential measurement though a hair and air interface; the interface presenting a high and variable source impedance coupling to the scalp; and
  a plurality of preamplifiers coupled to a respective one of the sensors; wherein each preamplifier is adapted to have an input impedance significantly higher than the impedance presented by the sensor source interface; wherein the preamplifier receives the raw scalp potential measurement and produces a preamplified scalp potential measurement for producing a pre-amplified scalp potential measurement.

The sensor source interface impedance is preferably presented by any contact medium, scalp, and underlying tissues.

The input impedance is preferably active and increased by the application of feedback.

The preamplifier preferably includes a wideband high impedance input, and an active biasing network, adapted to present an input impedance of greater than 10 Peta-Ohms from 0.01 Hz to 400 Hz. More preferably, the preamplifier includes a high-gain low-noise rail-to-rail FET input operational amplifier with an input impedance of 10 Tera Ohms and a shielded feedback and biasing network for presenting the input impedance.

Preferably, the apparatus further comprises:
  a common mode filter amplifier coupled to the pre-amplifier, wherein the common mode filter is adapted to cancel a substantial component of common mode signal and noise included in the pre-amplified scalp potential measurement thereby to produce a common mode cancelled scalp potential measurement; and
  an RF suppression system for suppressing RF noise of the common mode cancelled scalp potential measurement to produce an RF suppressed scalp potential measurement.

The common mode filter amplifier and the RF suppression system are preferably adapted to preserve a substantially common gain, phase and delay across each scalp potential measurement signal path.

Preferably, the apparatus further comprises:
  a differential amplifier system for amplifying the RF suppressed scalp potential measurement to produce an amplified scalp potential measurement; and;
  a band pass filter for filtering the amplified scalp potential measurement to substantially minimise aliasing effects during subsequent digitisation.

The differential amplifier system and the band pass filter are preferably adapted to preserve a substantially common gain, phase and delay across each scalp potential measurement signal path.

The band pass filter is preferably in the form of a low frequency transient high pass filter and a high frequency anti-aliasing low pass filer. More preferably, the band pass filter is adapted to provide suitable low frequency transient suppression and further adapted to provide attenuation greater than half a quantisation level at a Nyquist frequency for a predetermined analog-to-digital converter. Most preferably, the band pass filter is a sixth order symmetrical band pass filtering amplifier with a pass band of 1 Hz to 40 Hz.

Preferably, an input to the differential amplifier is selectable from any one of a set of signals including a common reference signal, an averaged signal and a pre-amplified and buffered sensor signal.

Preferably, the apparatus further comprises:
  a digitiser for digitising one or more scalp potential measurements; and
  a first processor for performing signal processing on one or more scalp potential measurements and producing an output signal.

The output signal is preferably transmitted wirelessly to a second processor.

Preferably, the apparatus further comprises a channel interconnection module adapted to suppress inter-channel RF interference between each scalp potential measurement signal path.

The channel interconnection module is adapted to select a scalp potential measurement mode from the set comprising: channel to reference-channel mode, channel to channel-average mode and channel to channel differential mode.

According to a second aspect of the invention there is provided a method for scalp potential measuring comprising the steps of:
- receiving raw scalp potential measurement at the sensor wherein the measurement is taken though hair and air; and
- pre-amplifying the raw scalp potential measurement with a high input impedance amplifier to produce a pre-amplified scalp potential measurement.

Preferably, the method further comprises the steps of:
- cancelling a substantial component common mode signal and noise of the pre-amplified scalp potential measurement to produce a common mode cancelled scalp potential measurement; and
- suppressing RF noise of the common mode cancelled scalp potential measurement to produce an RF suppressed scalp potential measurement.

Preferably, the method further comprises the step of amplifying the RF suppressed scalp potential measurement to produce an amplified scalp potential measurement for digitisation.

Preferably, the method further comprises the steps of:
- applying a band pass transient and anti-aliasing filtering of the amplified scalp potential measurement to produce an anti-aliased scalp potential measurement for digitisation;
- digitising the anti-aliased scalp potential measurement to produce a sequence of digitised scalp potential values.
- processing the sequence of digitised scalp potential values to produce a scalp potential waveform signal; and
- producing a measurement waveform.

Preferably, the method further comprises the step of transmitting an output signal over a wireless connection for receiving by a second processor.

Receiving raw scalp potential measurement is preferably measured though a hair and air interface; the interface presenting a high and variable source impedance coupling to the scalp; and the pre-amplifier is adapted to have an input impedance significantly higher than the presented the source interface. Preferably, the input impedance is active and increased by the step of applying feedback.

According to a third aspect of the invention there is provided a method for scalp potential measuring comprising the steps of:
- receiving an input raw scalp potential signal from a plurality of sensors for defining a respective plurality of channels;
- selecting a measurement mode configuration from a set comprising: channel to reference-channel mode, channel to channel-average mode and channel to channel differential mode;
- biasing the input signal while maintaining high input impedance;
- matching channel gain before differentially deriving a channel signal;
- suppressing radio frequency interference of the channel signal while maintaining gain and phase matching as a further step in providing a processed channel signal;
- suppressing common mode signal interference of the channel signal as a further step in providing the processed channel signal;
- band pass filtering the channel signal as a further step in providing the processed channel signal; and
- digitising the processed channel signal for providing a digital scalp potential measurement signal indicative of the input signal measured according to the selected measurement mode.

The high input impedance is preferably provided by a pre-amplifier including a high input impedance amplifier for amplifying the raw scalp potential measurement to produce a pre-amplified scalp potential measurement. The input impedance is preferably significantly higher than the impedance associated with a source interface presented to the sensor. The source interface impedance is preferably presented by any contact medium, scalp, and underlying tissues. Preferably, the input impedance is active and increased by the application of feedback. The preamplifier preferably includes a wideband high impedance input, and an active biasing network, adapted to present an input impedance of greater than 10 Peta-Ohms from 0.01 Hz to 400 Hz.

According to a further aspect of the invention there is provided an apparatus for scalp potential measuring comprising:
- a plurality of sensors, one of which may be considered as a difference, reference or common, adapted to measure a raw scalp potential measurement though hair and air interface; the interface presenting a high and variable source impedance coupling to the scalp; and
- a pre-amplifier coupled to the sensors; wherein the pre-amplifier is adapted to have an input impedance significantly higher than that presented by the source interface; wherein the pre-amplifier receives the raw scalp potential measurement and produces a pre-amplified scalp potential measurement.

BRIEF DESCRIPTION OF THE DRAWINGS

A preferred embodiment will now be described, by way of example only, with reference to the accompanying drawings in which.

DETAILED DESCRIPTION

Figure 1:
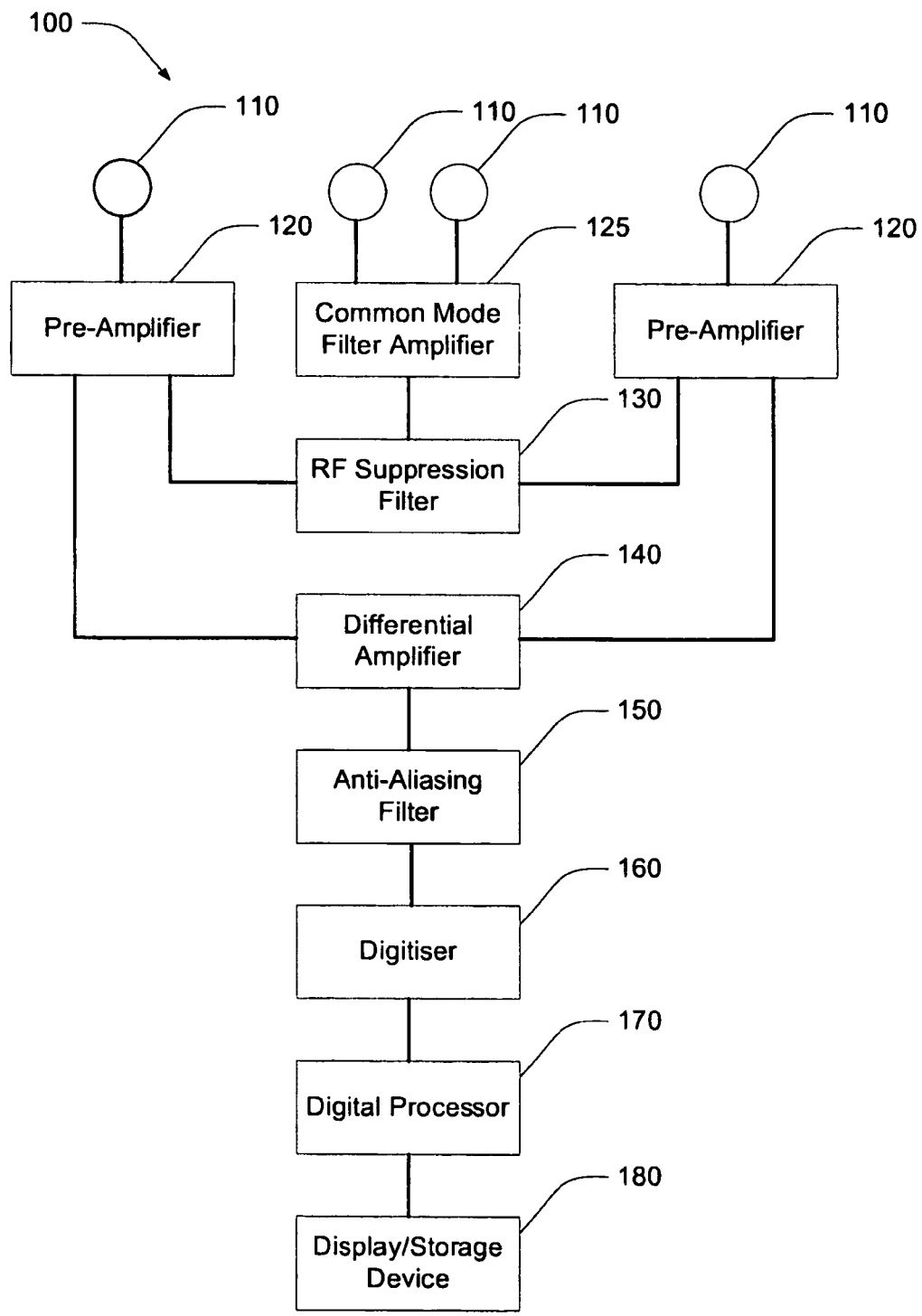
FIG. 1 is an example block diagram of an apparatus for measuring scalp potential.

Referring to the drawings, preferred embodiments of a method and apparatus for measuring scalp potential is disclosed.

The following embodiments provide a method and apparatus for processing signals from the sensor preferably in for form of an electrode, such that measurement of scalp voltage potentials is performed with relatively little or no hair and skin preparation. This reduces the ongoing need of conventional EEG measurement for exfoliating dead stratified epithelial cells, or the application of abrasive or conductive jells. It would be appreciated that a sensor these embodiments is preferably an electrode. It would be further appreciated that a sensor may be a passive or active device.

Referring initially to FIG. 1, an example block diagram 100 of an embodiment includes sensors (or electrodes) 110, pre-amplifier 120, common mode filter amplifier 125, RF suppression filter 130, differential amplifier 140, transient and anti-aliasing filer 150, digitiser 160, a digital processor 170, and a display or storage device 180. In this embodiment the differential amplifier 140 amplifies the difference between two sensor signals of which one may be considered as a selected common or reference signal.

Figure 2:
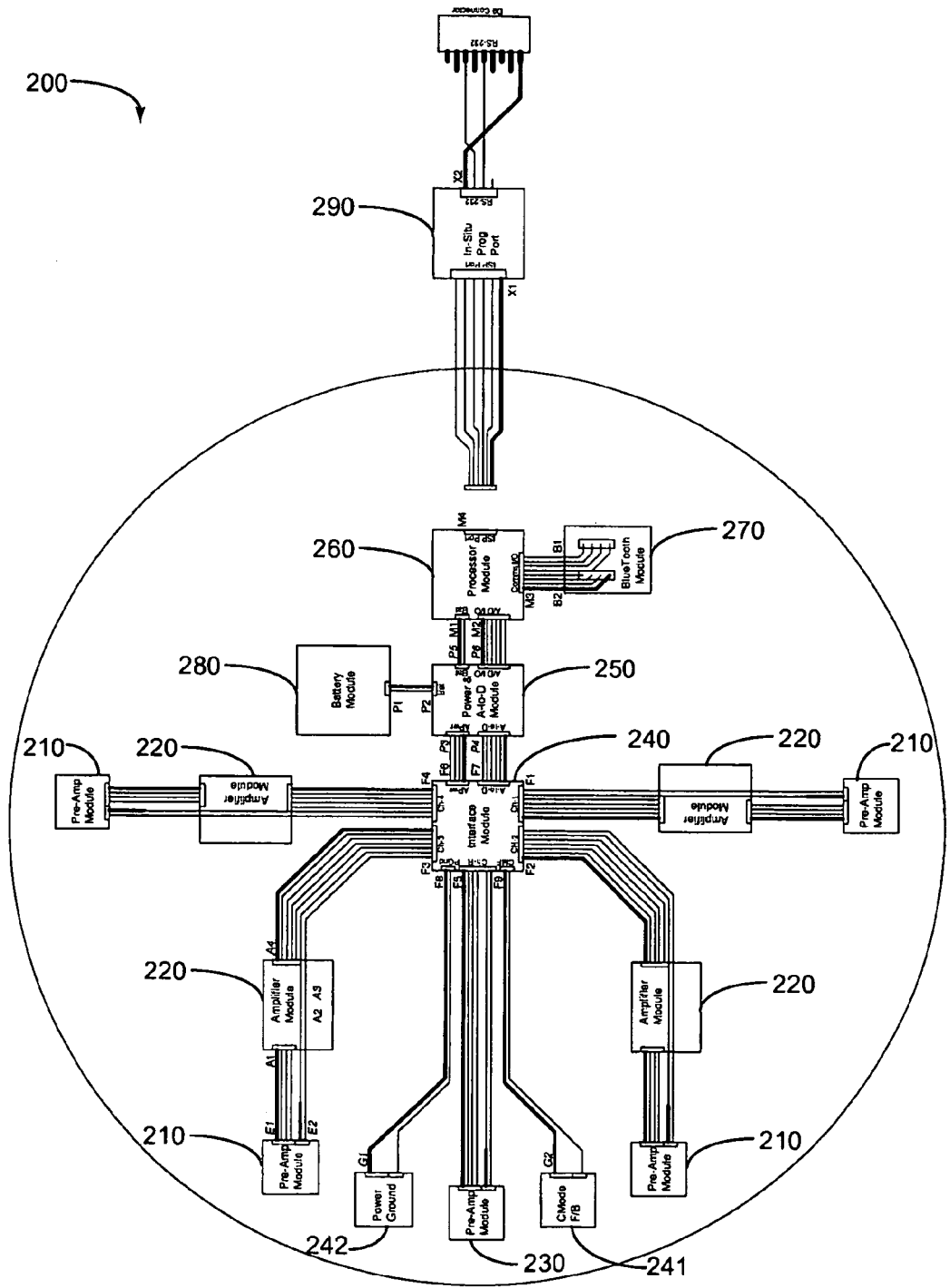
FIG. 2 is an example high-level schematic view of the apparatus according to FIG. 1.

FIG. 2 shows a high-level circuit schematic 200 of an embodiment having 4 input sensors. Each input sensor has an associated pre-amplifier module 210. These pre-amplifier modules provide a pre-amplifier and an RF suppression filter. Each preamplifier module is coupled to a respective amplifier module 220.

In this embodiment each amplifier module 220 provides a differential amplifier and an anti-aliasing filter in the form of a band pass amplifier. Preferably the differential amplifier selectively amplifies the difference between either a reference signal, an average of the input or another input signal. The band pass amplifier is configured to performing anti-aliasing filtering of the signal. A separate reference preamplifier module 230 provides the buffered reference signal for the system.

The output of these amplifier modules 220 and reference preamplifier module 230 are connected via an interface module 240, which further directs the signals to a power and analogue to digital converter module 250. This interface module 240 also provides a common mode feedback amplifier, which drives the common mode feedback sensor 241, and a signal reference buffer, which drives the power ground sensor 242.

The power and analogue to digital converter module 250 time samples and quantises each measured signal. This time sampled and quantised signal os presented to a processor module 260. The processor module performs further processing on the sampled signals to produce scalp potential measurements for output. Results produced by the processor module are output via the blue tooth module 270.

Other modules are also provided. A battery module 280 provides a staple supply of power to the system and includes a battery charging system. An in-situ programming port 290 is also shown as a means for programming and communicating with the processor module 260.

Figure 3:
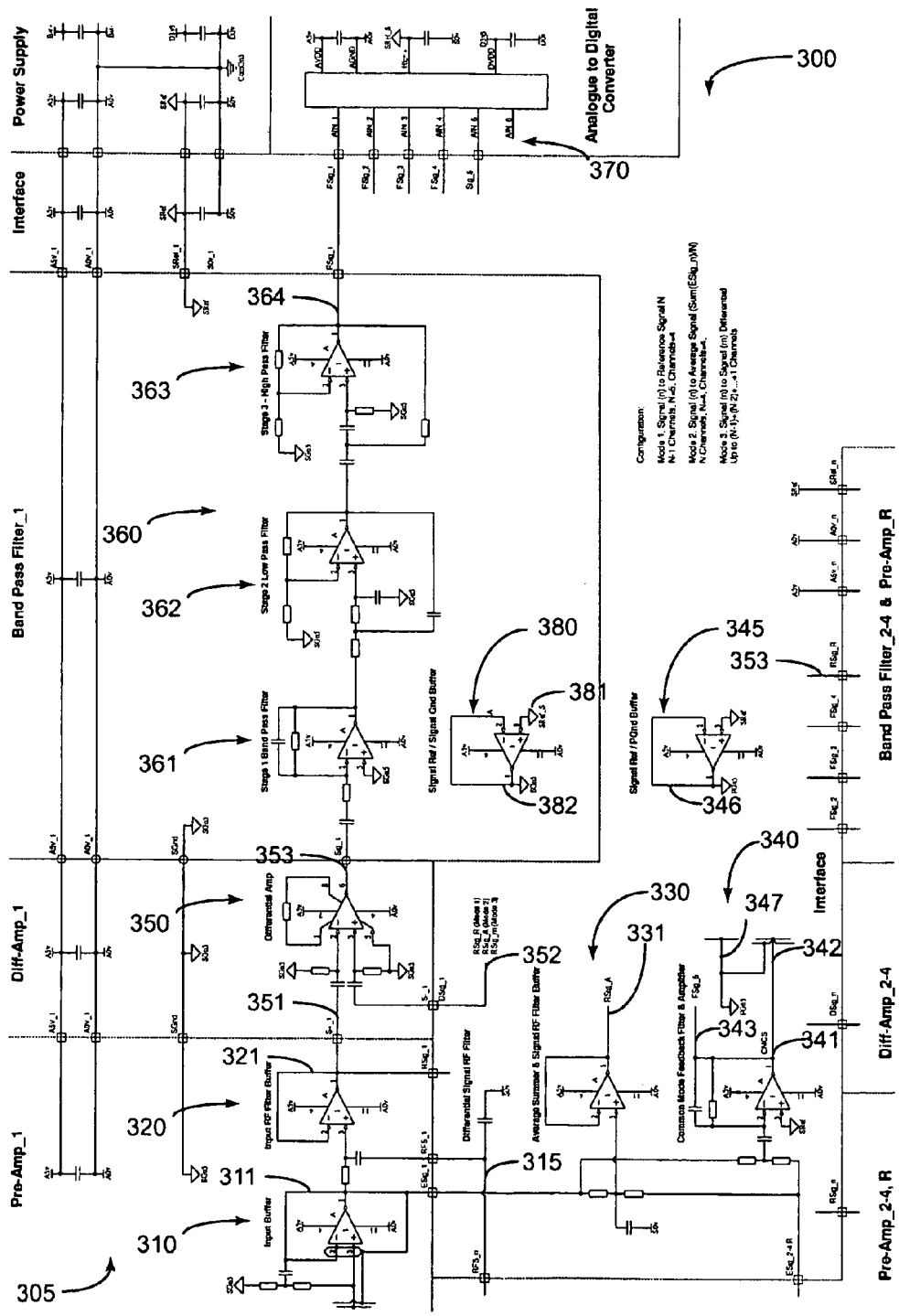
FIG. 3 is an example high-level schematic view of the analog circuitry according to FIG. 2.

FIG. 3 shows an example overview schematic of the analogue signal processing 300. This high level schematic focuses on the signal conditioning of a single channel. The analogue processing represented by this schematic is repeated for each input sensor signal.

In this embodiment, an input sensor signal is processed by a pre-amplifier 305. Firstly, the sensor signal is buffered by a unity gain buffer 310, with feedback adapted to boosts the input impedance. In this embodiment the input impedance is active, and increased by the application of feedback. A buffered sensor signal 311 is extended to an average summer and signal RF filter buffer 330 and the common mode feedback filter and amplifier 340. The buffered sensor signal 311 is passed through a differential mode low pass filter 315 to suppress RF interference signals and then buffered by a second unity gain buffer 320. The pre-amplified and buffered signal 321 is extended to the interface module as a reference signal 351 and is passed to a differential amplifier 350.

This schematic further shows all of the buffered input sensor signals 311 are preferably averaged and buffered by the average summer and signal RF filter buffer 330 to produce an average signal 331. This averaging amplifier comprises a summing low pass RF filter network buffered by a low noise unit-gain amplifier to produce an output average signal 331 being average all input sensor signals. This average signal 331 is used for a "channel to channel average" measurement mode, (MODE2 below). This circuit has selected phase shift and signal delay characteristics to match the differential RF filter 315.

A Common mode feedback filter and amplifier 340 is used to suppress common mode signals and boost common mode to differential mode rejection characteristics. This feedback amplifier comprises a summing network forming part of the filter feedback network around the amplifier. The feedback amplifier generates a high gain negative feedback common mode cancelling output 341, which is applied to the common mode feedback sensor 342 and is extended as channel 5 signal 343 to the analogue-to-digital converter module 380.

In this embodiment, a signal reference/power ground unity gain buffer 345 produces the power ground output 346 which drives the power ground sensor 347. This completes an external feedback network, which is comprised of the contact impedances of all of the feedback, power ground and sensors and the subcutaneous impedances internal to the scalp and underlying tissues.

The pre-amplified and buffered signal 351 is AC coupled and applied to a differential amplifier 350. In this embodiment, the other differential amplifier input signal 352 is selected from either a common reference signal 353 (MODE 1), the averaged signal 321 (MODE 2) or another pre-amplified and buffered signal 321 (MODE 3). The selected signal 352 is then AC coupled and applied to the differential amplifier. The differential amplifier 350 amplifies the difference between the pre-amplified and buffered signal 351 and the selected signal 352 and produces a differential signal 353. In this embodiment, an input to the differential amplifier is selectable from any one or more of the set of signals including a common reference signal, an averaged signal and a pre-amplified and buffered sensor signal.

A different number of signals are possible depending on the mode selected. These possibilities are represented in the table below, based on N input signals.

| Mode | Signals based on N sensor measurements |
| --- | --- |
| Mode 1 | Signal(n) referenced to SIG_REF<br>N possible signals |
| Mode 2 | Signal(n) referenced to Average Signal<br>N possible signals |
| Mode 3 | Signal(n) referenced to Signal(m)<br>(N − 1) + (N − 2) + . . . + 1 possible signals |

The differential signal 353 is then filtered by a band pass filter stage 360, for reducing aliasing artefacts arising in later digitisation of the signal. In this embodiment the filter stage 360 comprises three stages in series. The stages comprise a band pass filter 361, a low pass filter 362 and a high pass filter 363. The band-pass filtered signal 364 is then provided to an analogue-to-digital converter module 370.

A signal reference/signal ground buffer 370 isolates and buffers the signal reference 381, producing the signal ground 382 which is extended to the band pass filter, differential amplifier and pre-amplifier circuits.

A more detailed disclosure of modules that comprise an embodiment now follows.

Figure 4:
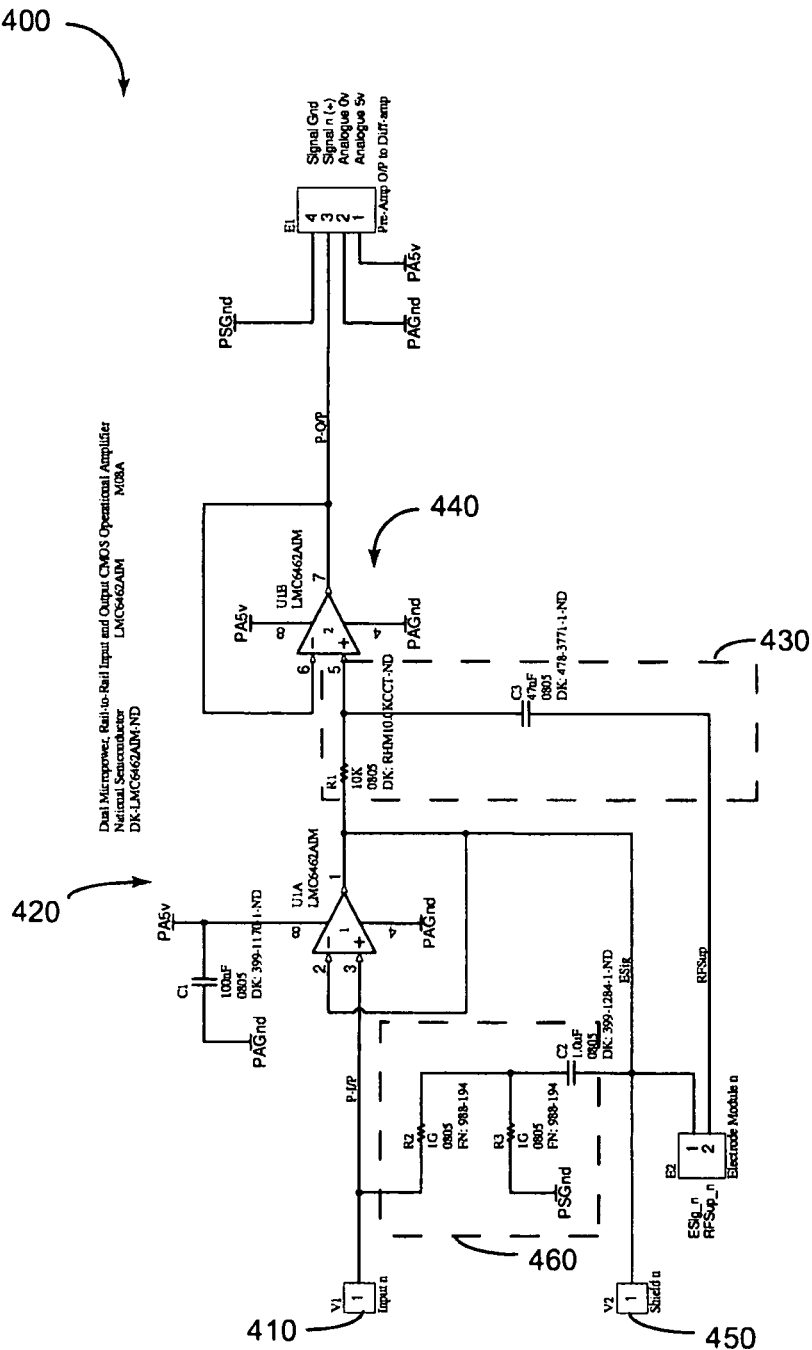
FIG. 4 is an example schematic view of a pre-amplifier module according to FIG. 2.

FIG. 4 shows a schematic diagram of the pre-amplifier module 400. An input sensor signal 410 is applied to a unit gain buffer 420, a low pass filter 430 and a unit gain buffer 440 in series.

The shield for the input sensor is actively driven by a shield signal 450. This shield signal is principally driven by the output of the unit gain buffer 420.

The buffer 420 is biased by the feedback network 460 and presents a DC input impedance of 2 G Ohms for the input sensor signal 410. The AC input impedance is bolstered by the feedback network, being multiplied by the open loop gain of the buffer amplifier. In this embodiment, the circuit is selected to present a minimum of 1 Peta Ohms ($10^{15}$ Ohms) between 1 Hz and 40 Hz. This AC input impedance is preferably significantly higher than the source interface, presented by any contact medium, scalp, and underlying tissues.

Primarily, resistive coupling exists between the scalp and the input sensors. For direct contact with the skin, the coupling has relatively low source impedance. Where the sensor is separated from the skin by hair, perspiration may form an electrolytic conductive path and present still relatively low source impedance. This input impedance typically increases when presented with an air gap between the sensor and scalp.

The unit gain preamplifier 420 is provided with comparably high and suitably matched input impedance, which enables improved detection of the scalp signals. Techniques have been developed for presenting this high input impedance, through providing precision channel gain matching and signal amplification.

Preferably, the preamplifier 420 has a wideband high impedance input and active biasing network, which presents greater than 10 Peta-Ohms ($10^{16}$ Ohms) from 0.01 Hz to 400 Hz. A high gain, low noise, rail-to-rail FET input operational amplifier, with an input impedance of 10 Tera Ohms ($10^{19}$ Ohms), in conjunction with a shielded feedback and biasing network is used to present the desired input impedance. This is used to reduce the effect caused by the variability of source impedances as a result of diverse source characteristics created by a combination of factors including skin, hair, and humidity conditions. It also ensures high precision preamplifier gain matching between channels, prior to subsequent signal processing.

In this embodiment, the feedback and biasing network for the high impedance preamplifier uses unity gain positive AC feedback to the centre of two high Ohmic DC biasing resistors. Mathematical analysis is performed to provide stability criteria for avoiding oscillation. This network maintains the high input impedance across the system bandwidth so as to preferably preserve the high precision gain matching between channels. A unity gain positive feedback is also used to drive active shielding of the preamplifier inputs and the sensor.

The RF suppression circuit 430, in conjunction with the network connection 625 (shown in FIG. 6), preferably completes the RF filter and provides both differential and common mode suppression of RF interference while maintaining high precision gain matching between channels and compensating for phase shifts and delays inherent in common RF suppression techniques.

As shown, this RF suppression network uses a 'delta' configuration, rather than a 'pi' configuration typically used in conventional differential designs. This structure facilitates RF suppression across the multi-channel system, without affecting the high precision gain matching between channels.

In this embodiment, the output of the RF suppression filter is buffered by a low noise unity-gain buffer 440 before providing the final output signal to the amplifier module. The phase characteristics of this arrangement preferably match the phase shift and signal delay introduced by the averaging amplifier. The arrangement for this RF suppression network isolates the differential RF suppression network from a high impedance-biasing network of the amplifier stage, and substantially preserves the high precision gain matching between channels.

Figure 5:
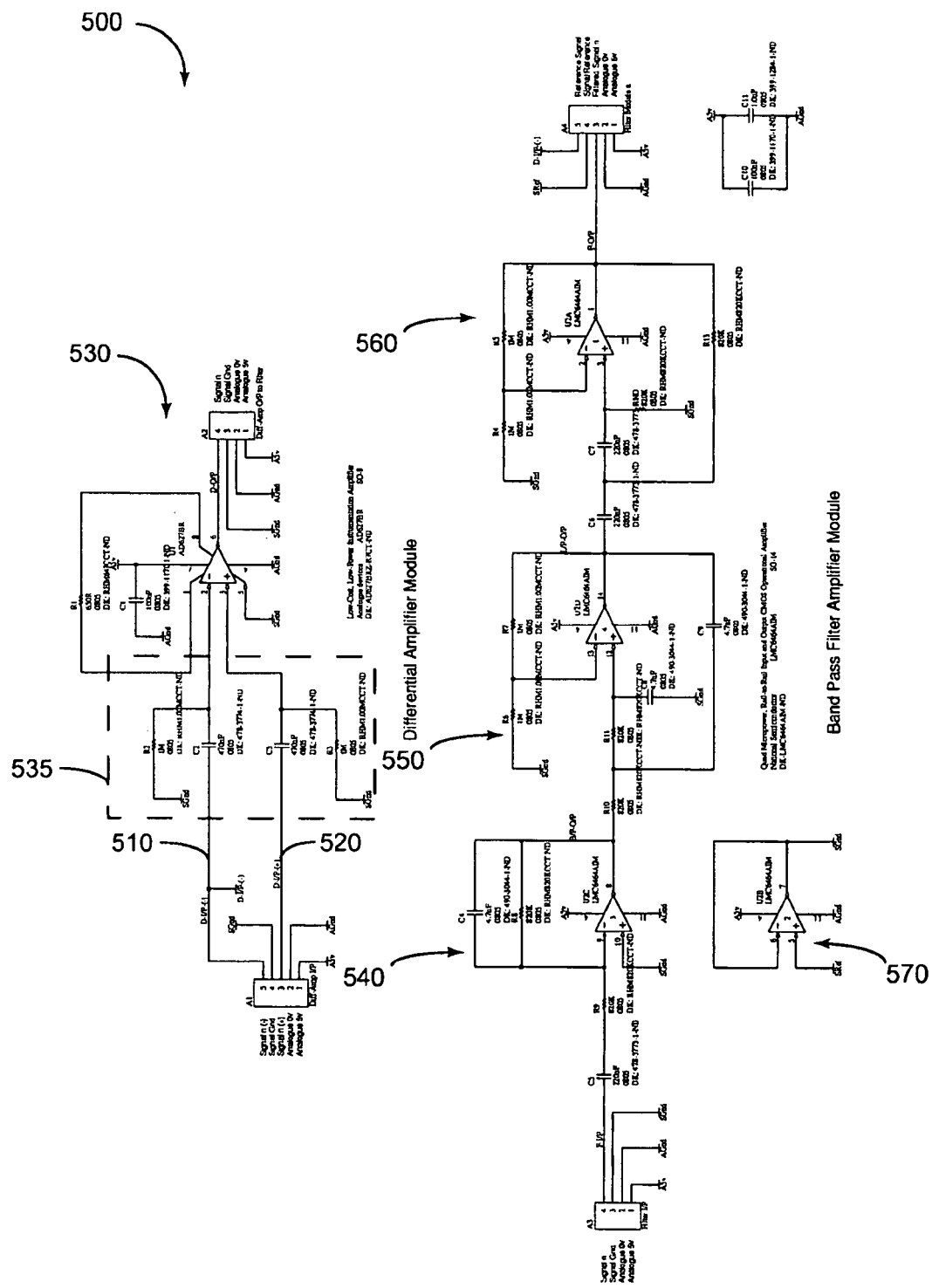
FIG. 5 is an example schematic view of an amplifier module according to FIG. 2.

FIG. 5 shows an example schematic diagram of an amplifier module 500. This amplifier module applies an input signal 510, as produced by the circuit shown in FIG. 4, and a selected signal 520 to a series connection of a differential amplifier 530, a band pass filter 540, a low pass filter 550 and a high pass filter 560.

The differential amplifier 530 preferably comprises a high precision, high gain, low noise instrument differential amplifier integrated circuit. This amplifier is used to selectively boost the differential signal while rejecting the common mode signal. A high impedance biasing and AC coupling network 535 is selected to maintain the frequency response and high precision gain matching between channels.

In this embodiment, the instrument amplifier gain is set to provide a ±1 mV dynamic range when referenced to the sensor input. The amplification gain is intended to be set such that the amplified output signal is maintained within the dynamic voltage range of the digitisation stage. The gain of the intermediary anti-aliasing filter must therefore be included in this calculation.

Anti-aliasing filtering is preferably performed by the three stage band pass filter comprised of the stage 1 band pass filter 540, stage 2 low pass filter 550 and stage 3 high pass filter 560. The low-pass filtering characteristic of band pass filter reduces the aliasing effect caused by discrete time sampling of the signal. It is preferable that the filter attenuation, at and above the Nyquist frequency, reduces the signal level to be less than the quantisation level of the following digitising system. Therefore the characteristics of the aliasing-filter and the digitisation system must be considered together once design constraints are established.

The high pass filtering characteristic of the band pass filter 540 reduces the effects of low frequency transients, resulting from sensor movement, which would otherwise generate signals greater then the dynamic range of the filter and following digitization stage.

In this embodiment, a sixth order symmetrical band pass filtering amplifier with a pass band of 1 Hz to 40 Hz is used. This filter is chosen to provide attenuation better than half a quantisation level at a Nyquist frequency that can be readily obtained using a low power analogue-to-digital converter and to provide suitable low frequency transient suppression.

A signal reference unity gain buffer 570 provides substantial channel isolation and fan out for the signal ground to the filter, differential amplifier and the pre-amplifier stages of the associated channel.

Figure 6:
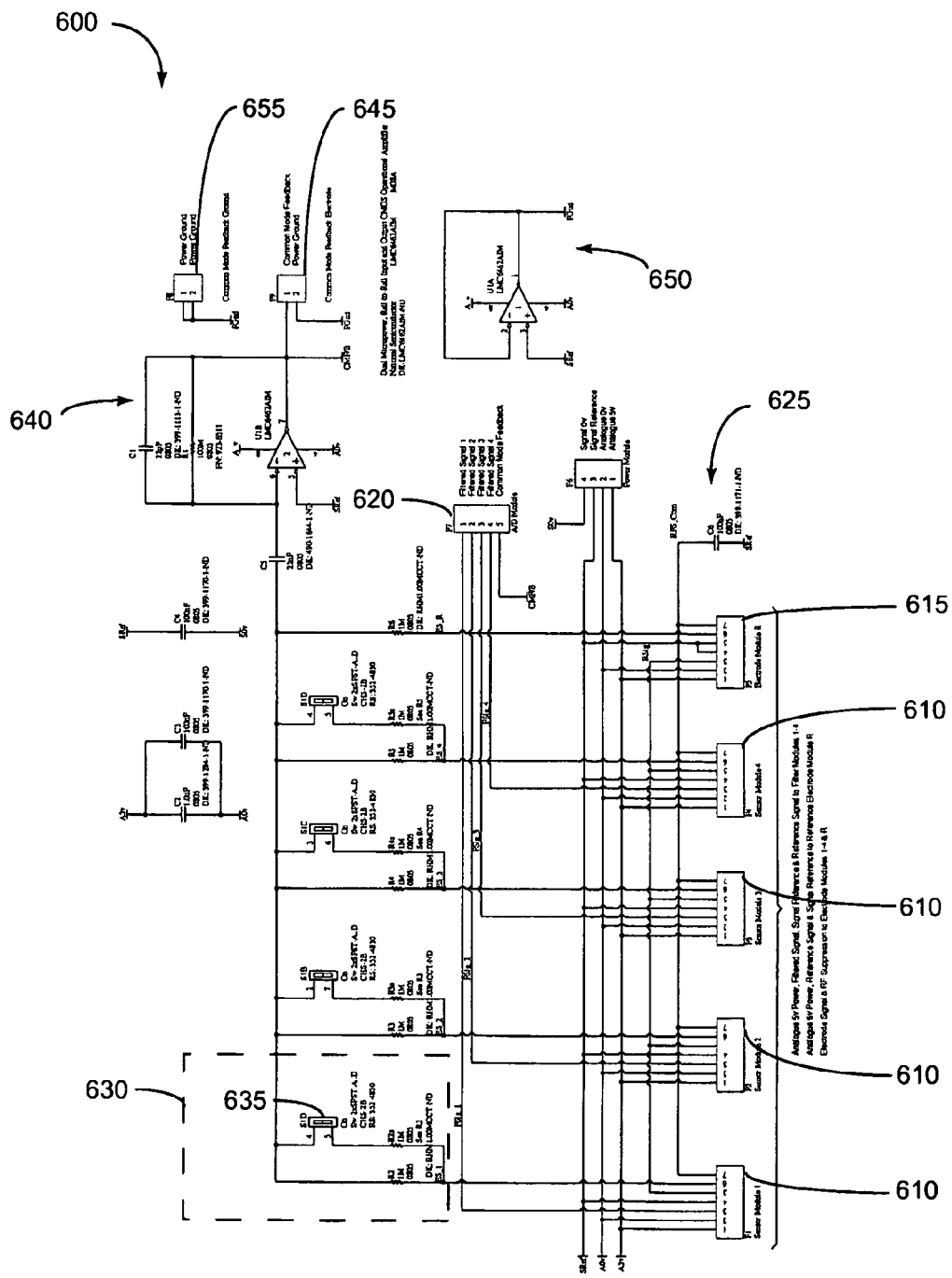
FIG. 6 is an example schematic view of an interface module according to FIG. 2.

FIG. 6 shows an example schematic diagram of an interface module 600. This schematic diagram shows the preferred interfacing of the signals, for channel to reference channel measurement (MODE 1), from each of the amplifier modules for each sensor module 610 to output signals 620 and a reference pre-amplifier module 615. These output signals 620 form the input to an analogue-to-digital converter. The reference signal is feed from the reference pre-amplifier module 615 to each of the sensor modules 610.

In another embodiment, alternative configurations are used to implement signal to signal average measurement (MODE 2) or signal to signal measurement (MODE 3). The average summer and signal RF filter buffer 330 is not shown in FIG. 6.

The RF network connection 625, across the sensor modules 610 and the reference pre-amplifier module 615, completes the differential RF suppression filter.

A common mode feedback filter and amplifier 640 is incorporated into this interface module. This common mode feedback filter and amplifier 640 provides the common mode cancelling output 645, which connects to the common mode feedback sensor 241.

A signal reference unity gain buffer 650 is incorporated into this interface module. This signal reference unity gain buffer 650 provides isolation and power drive to the power ground output 655, which connects to the power ground sensor 242. This completes the common mode cancellation network.

This schematic diagram further shows alternative construction options for either hardwired or switch selectable input connections to the to the common mode feedback module 640. In this embodiment, a hardwired option is fitted with resistors "Rn" only, whereas a switch selectable option is fitted with resistors "Rns" and series switches. The switch selectable option enables selected inputs to be connected to or isolation from the common mode feedback filter and amplifier 640, by engaging or disengaging the electronic switch 635.

Figure 7:
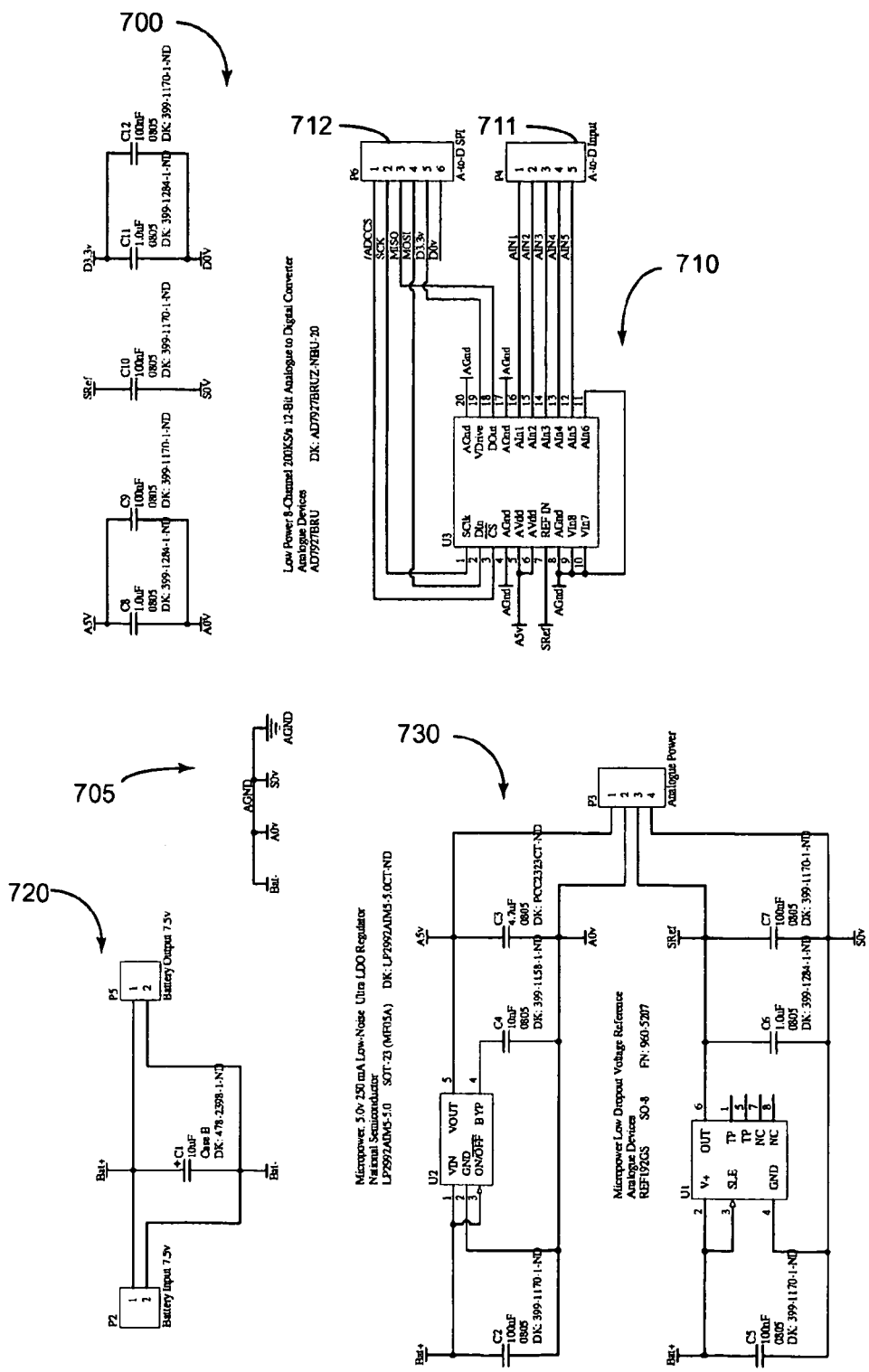
FIG. 7 is an example schematic view of an analogue-to-digital module according to FIG. 2.

FIG. 7 shows an example schematic diagram for a power and analogue-to-digital converter module 700. This module includes a common ground point "AGND" 705, an analogue to digital converter circuit 710, battery power filter circuit 720 and power and signal reference circuit 730.

The common ground point "AGND" 705 is preferably formed by a ground plane associated with the analogue part of the analogue-to-digital converter. Separate ground connections are preferably run independently for battery negative, analogue supply zero volts, signal reference zero volts and digital ground in the digital modules.

The analogue to digital converter (ADC) circuit 710, time-samples and quantises the input signals 711 provided by the interface module described earlier. The ADC is categorised by its 'n' bit digital output 712 that is presented in a format that is compatible with the later processor module.

In this embodiment, the ADC has a Least Significant Bit (LSB) resolution of at least 0.5 uV and a full scale range of ±1 mV, when referenced to the sensor input. To provide this dynamic range a minimum of a twelve bit ADC is used. The output is presented in a Serial Peripheral Interface (SPI) format.

Therefore when designing the anti-aliasing filter to match the twelve bit ADC, at least 72 dB attenuation is required at the stop band frequency. A third order low pass Butterworth filter, with a cut-off frequency of 40 Hz, has an attenuation of 72 dB at 640 Hz. For no aliasing at the cut-off frequency 40 Hz, a sample rate of 680 samples per second is required. For no aliasing at the stop band frequency 640 Hz, a sample rate of 1280 samples per second is required.

Once the signals are digitised further processing is performed by the processor module.

Figure 8:
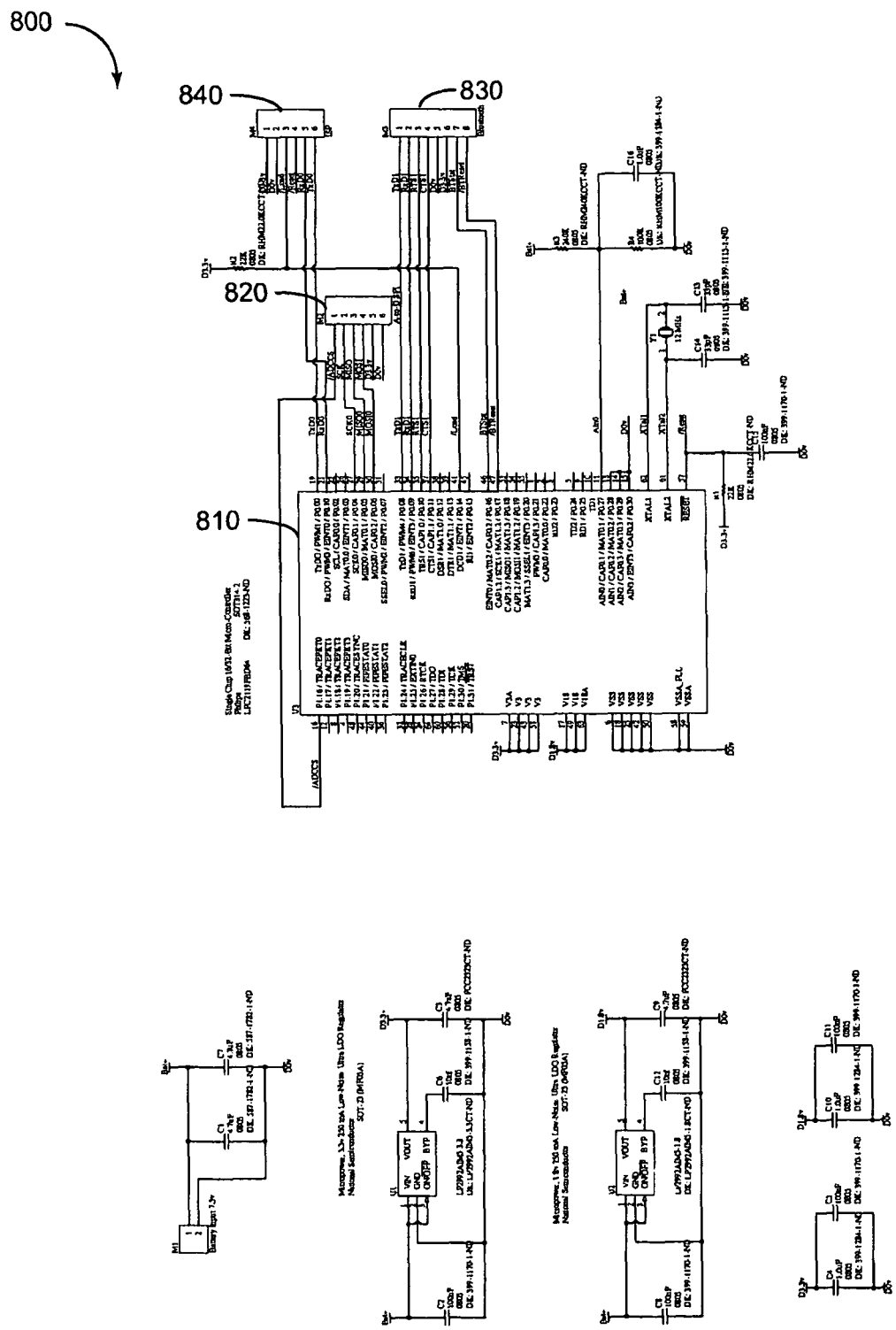
FIG. 8 is an example schematic view of a processor module according to FIG. 2.
Figure 9:
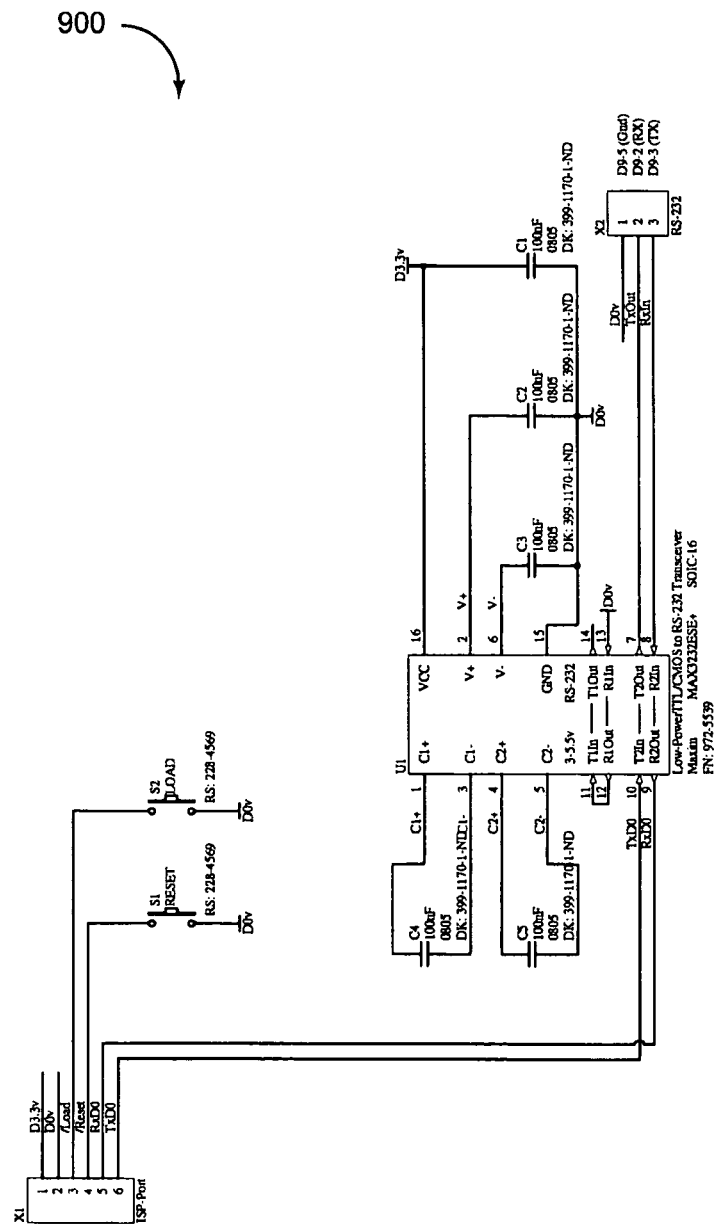
FIG. 9 is an example schematic view of an in situ programming port module according to FIG. 2.

FIGS. 8 and 9 show an example of a processing and wired communications modules of an embodiment. The processor module 800 includes a processor 810. This processor controls the analogue-to-digital converter and receives the signal from the analogue-to-digital converter via an SPI interface 820. In this embodiment, the signals may then be processed and analysed by the processor. The raw signal may also be transmitted to an external processor for storage and further processing. Typical internal and external processing includes sample decimation, fast Fourier transformations and application programs. The firmware functionality can be command configured.

In this embodiment the processor can communicate with other devices, including the transmitting of raw and result data, via a blue tooth interface port 830 or RS232 interface port 840. The RS232 interface port 840 also supports In Service Programming (ISP) for software loading and update.

FIG. 9 shows an example schematic diagram for the RS232 interface module 900. The RS232 interface module 900 facilitates logic to RS232 level translation and provides reset and software load initiation.

A channel interconnection circuit facilitates a number of features for measurement modes as well as enabling inter-channel RF suppression and reference signal selection. Scalp voltage potentials can be measured in three modes:

(MODE 1) Channel to Reference Channel Mode.
(MODE 2) Channel to Channel Average Mode.
(MODE 3) Channel to Channel Differential Mode.

In this embodiment, the interface module illustrated in FIG. 6 is hardwired for Channel to Reference Channel (Mode 1) only. In other embodiments, the interface module can be designed for other modes, either hardwired individually or selectable, as depicted in FIG. 3.

Irrespective of which mode is used to measure signals, in other embodiments, digital signal processing can be used to reconstruct the other measurement mode signals.

Figure 10:
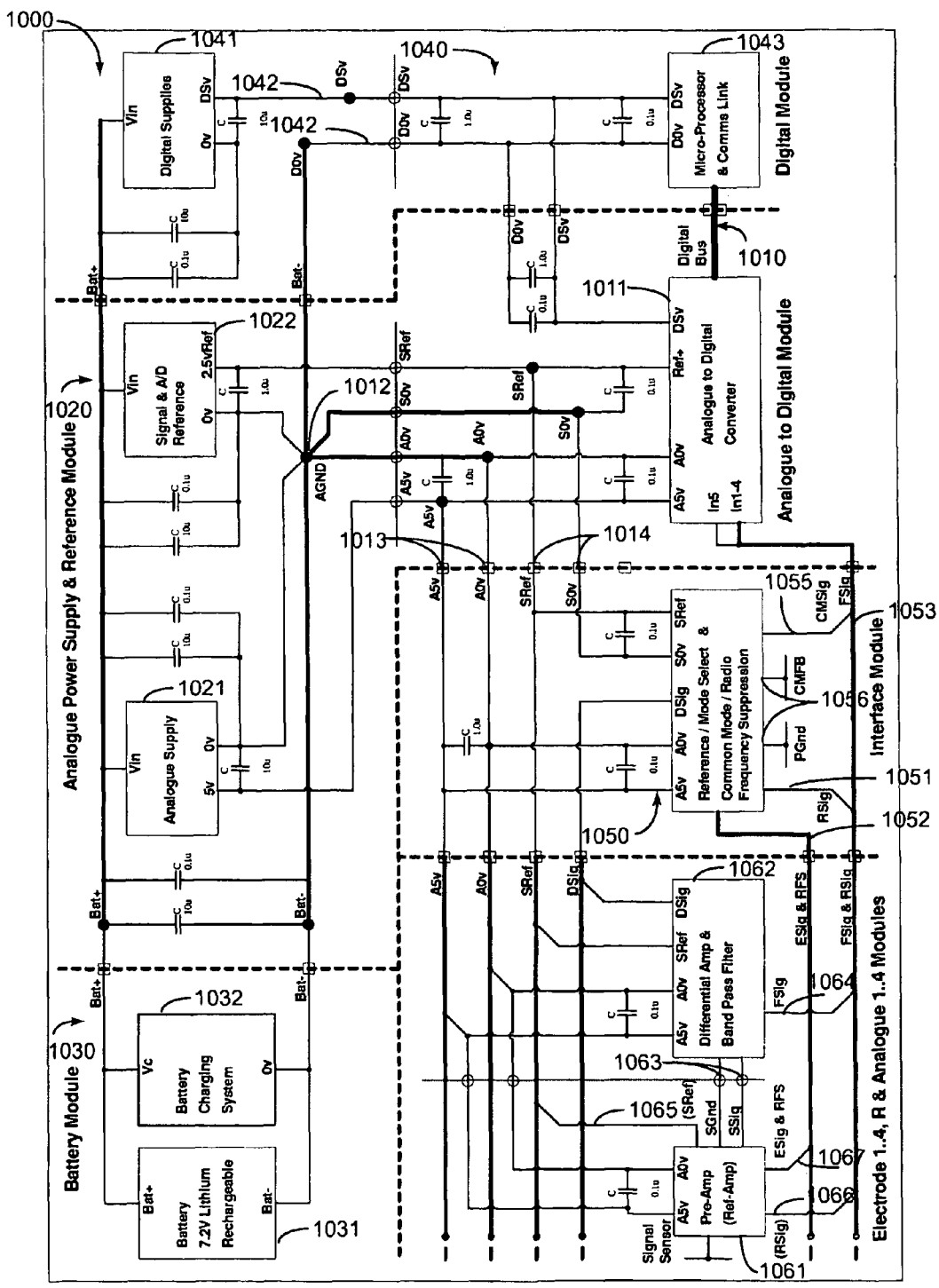
FIG. 10 is an example schematic view of a signal, power and ground configuration according to FIG. 2 and FIG. 3.

FIG. 10 shows an example signal power and grounding configuration 1000, primarily addressing the analogue design of the system. The power and grounding configuration centres around the analogue-to-digital module 1010 and the analogue power supply and reference module 1020, consisting of the analogue supply 1021 and the signal and analogue-to-digital reference 1022, with independent input and output decoupling.

This analogue-to-digital module 1010 houses the analogue-to-digital converter 1011 and its associated common ground point 1012, seen as the common ground point 705 in FIG. 7. The analogue power 1013 is run independently and is decoupled with its own analogue zero volts. The signal reference 1014 is run independently and is decoupled with its own signal zero volts. This module receives the analogue signals "FSig" and "CMSig" 1015 from the interface module 1050 and connects to the processor in the digital modules 1040 via the digital bus 1016.

A battery module 1030 consists of a rechargeable battery 1031 and charging system 1032. Battery positive and negative connect to the analogue power supply and reference module 1020 and are extended to the digital modules 1040. In this embodiment the digital power supplies 1041 consist of separate 3.3 v and 1.8 v supplies, with independent input and output decoupling. The digital power 1042 is run independently to the analogue-to-digital converter 1011 and to the digital circuits 1043 and is decoupled with its own digital zero volts.

An interface module 1050 distributes the analogue power 1013 and signal and analogue-to-digital reference 1014, independently decoupled, each with its own zero volts, to a pre-amplifier and analogue modules 1060. This module also receives a reference signal "RSig" 1051, sensor signals "ESig" and a RF suppression connections "RFS" 1052 from the pre-amplifier and analogue modules 1060 and passes filtered and amplified sensor signals "FSig" 1053 to channels 1 to 4 of the analogue-to-digital converter 1011 in the analogue-to digital module 1010. The reference signal is extended back as a different amplifier reference signal "DSig" 1054 to differential amplifiers 1061 in pre-amplifier and analogue modules 1060. The common mode feedback signal 1055 is extended to channel 5 of the analogue-to-digital converter 1011 in the analogue-to digital module 1010 and provides the common mode feedback via common mode feedback and power ground sensors 1056.

In this embodiment, the pre-amplifier and analogue modules 1060 are comprised of four sensor pre-amplifier modules 1061 paired with four analogue modules 1062 and a standalone reference pre-amplifier module 1061. The sensor pre-amplifier modules 1061 have sensor signal "SSig" and signal ground "SGnd" connections 1063 to the differential amplifier in the paired analogue modules 1062. The band bass filter in the paired analogue modules 1062 extends the filtered signal "FSig" 1064 to the interface module 1050. The reference pre-amplifier module 1061 receives signal reference "SRef" 1065 from the interface module 1050 and extends the reference signal "RSig" 1066 to the interface module 1050. The reference and sensor pre-amplifier modules 1061 extend the sensor signals "ESig" and the RF suppression connections "RFS" 1067 to the interface module 1050.

In each of the analogue stages careful selection must be observed such that the apparatus maintains a relatively low noise design, high common mode rejection and radio frequency rejection.

In this embodiment, low noise components are selected for the preamplifier and buffer operational amplifiers, the differential amplifier and the analogue to digital converter. Strategic signal, power, ground and decoupling schemes are also utilised. This embodiment further includes, a low-noise power supply and voltage reference circuits are used, along with separate signal and power grounds and power supply decoupling methods. Noise from high impedance components is also addressed using techniques for effectively attenuating noise introduced by these components.

In this embodiment, an active common mode cancellation feedback approach is used to improve the common mode rejection. A high gain negative feedback with 50 Hz to 60 Hz pre-emphasis is provided by a band pass filtering amplifier. This is realised using a two point connection to the source, in contrast to the usual method of single low gain actively driven connection.

In this embodiment, the feedback, power ground and sensors are typically configured with geometric symmetry to provide optimal common mode cancellation.

These embodiments of various apparatus for scalp potential measuring include:
(a) channel gain matching before differentially deriving each channel signal.
(b) input biasing while maintaining high input impedance and gain matching.
(c) radio frequency suppression in a multi-channel system while maintaining gain matching and compensating for phase shifts and signal delays.
(d) common mode signal rejection and cancellation, in particular, and power and radio frequency interference rejection.
(e) digitisation resolution, dynamic range and anti-aliasing.
(f) low noise and noise attenuation techniques.
(g) measurement mode configuration built into the method preserving the essential key elements.

Figure 11:
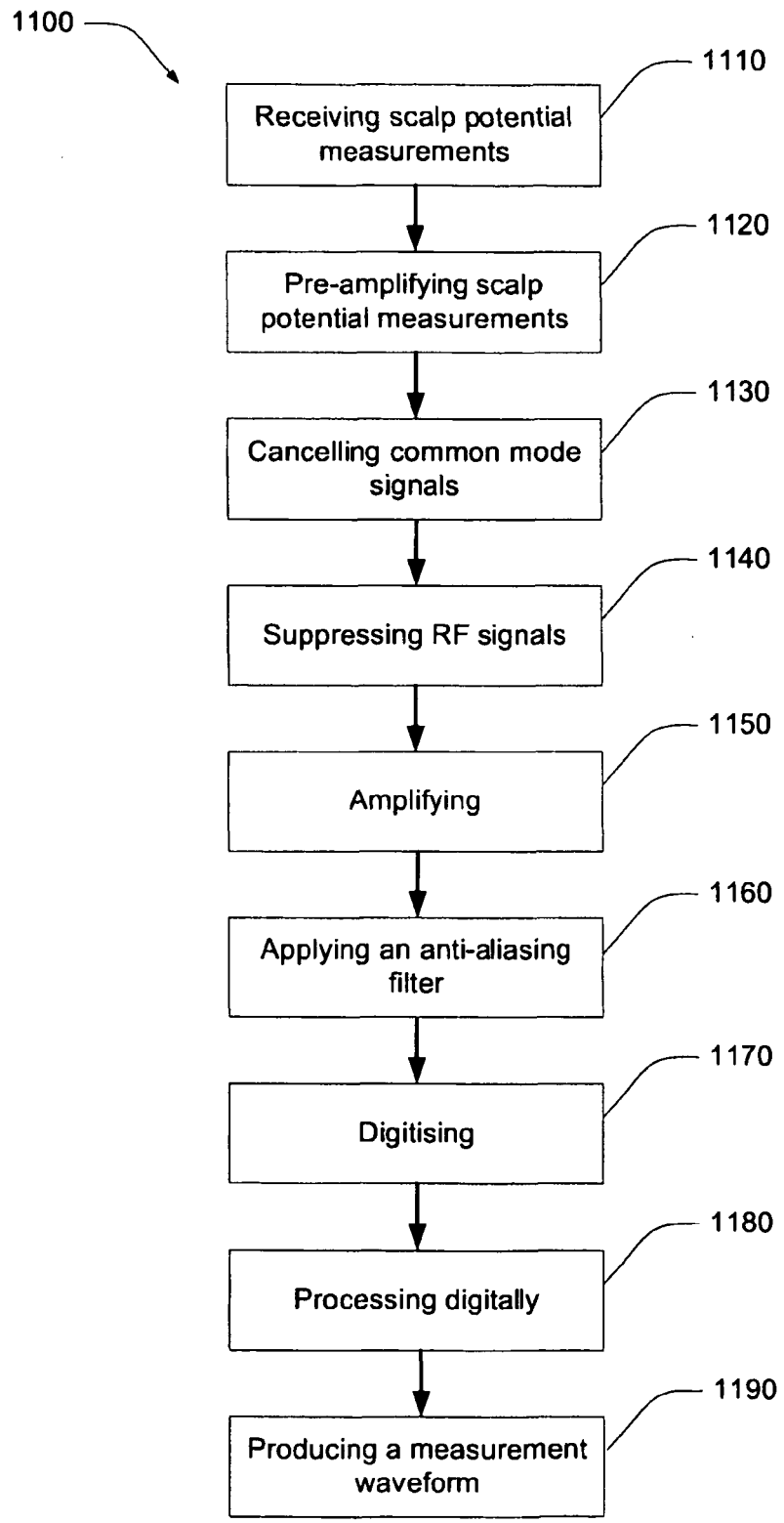
FIG. 11 is an example flow chart of a method for measuring scalp potential.

Referring to FIG. 11, a preferred method for measuring scalp potential 1100, according to any one of the previously described embodiments, includes:
(a) receiving raw scalp potential measurement at a sensor 1110;
(b) pre-amplifying the raw scalp potential measurement with matched high input impedance amplifiers 1120 to produce a pre-amplified scalp potential measurement for amplification;
(c) cancelling a substantial component of common mode noise 1130 of the pre-amplified scalp potential measurement to produce a common mode cancelled scalp potential measurement.
(d) suppressing RF noise 1140 of the common mode cancelled scalp potential measurement to produce an RF suppressed scalp potential measurement;
(e) amplifying 1150 of the RF suppressed scalp potential measurement to produce an amplified scalp potential measurement for digitisation;
(f) applying a band pass transient and anti-aliasing filtering of the amplified scalp potential measurement 1160 to produce a bandwidth limited scalp potential measurement for digitisation;
(g) digitising the bandwidth limited scalp potential measurement 1170 to produce a sequence of digitised scalp potential values;
(h) processing the sequence of digitised scalp potential values 1180 to produce a scalp potential waveform signal; and
(i) producing/storing a measurement waveform 1190.

This method typically allows the raw scalp potential measurement to be received 1110 at a sensor though hair without any scalp preparation or conductive gel being applied between the scalp and sensor. These raw scalp potential measurements are pre-amplified 1120 by an amplifier, with a substantially high input impedance and matched gain, phase and delay, to produce pre-amplified scalp potential measurements.

Preferably, cancelling a substantial component of the common mode signal noise 1130 of the pre-amplified scalp potential measurements produces a common mode cancelled scalp potential measurements, while preserving matched gain, phase and delay.

Suppressing RF noise 1140 of the common mode cancelled potential measurements to produce an RF suppressed scalp potential measurements, while preserving matched gain, phase and delay.

Amplifying 1150 of the RF suppressed scalp potential measurement to produce an amplified scalp potential measurement for digitisation.

Applying a band pass anti-aliasing filtering of the amplified scalp potential measurement 1160 to produce bandwidth limited scalp potential measurement for digitisation.

Digitising the bandwidth limited scalp potential measurement 1170 to produce a sequence of digitised scalp potential values.

Processing the sequence of digitised scalp potential values 1180 to produce a scalp potential waveform signal.

Producing/storing a measurement waveform 1190.

These measurements can be taken up to the life of the associated power source or storage capacity of the associated data recorder. The sensors and associated electronics may be concealed in a conventional head accessory, such as a baseball cap, or may be incorporated into a safety helmet.

The fidelity of the scalp potential measurements produced by the illustrated embodiments is sufficient to successfully classify benchmark mental states. These scalp potential measurements are considered comparable to traditional EEG measurements that typically require a stable conducting interface between the scalp and sensor, for analysis of certain mental states.

Analysis of scalp potential measurements from a person provides a means for determining the person's fatigue, or drowsiness, in real time. By providing this real time monitoring system that can be warn without specialised scalp preparation, this system could monitor a persons fatigue while operating equipment, such as motor vehicles or plan equipment.

This method and apparatus has been designed for mobile non-intrusive real-time scalp potential measurement. It is apparent that this can be used in a mobile or stationary environment. For real time processing data processing software could be included to further process the scalp potential measurement data. The data and signals can be communicated in a raw or processed state by wired or wireless data communications system. The electrical energy for powering these devices is provided in conventional means by a battery or wirelessly using an inductive loop arrangement. It will be further appreciated by those skilled in the art that the disclosed method and apparatus may be used in a clinical setting to remove the necessity for a scalp preparation step and reduce consultation times.

It will be appreciated that these embodiments are able to measure scalp potential though hair, with little or no scalp preparation.

Although the invention has been described with reference to specific examples, it will be appreciated by those skilled in the art that the invention may be embodied in many other forms.

Interpretation

In the context of this document, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not.

Unless specifically stated otherwise, as apparent from the following discussions, it is appreciated that throughout the specification discussions utilizing terms such as "processing," "computing," "calculating," "determining" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Reference throughout this specification to "this embodiment", "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

Similarly, it is to be noticed that the term coupled, when used in the claims, should not be interpreted as being limitative to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

What is claimed is:

1. A method for processing scalp potential signals comprising receiving an input raw scalp potential signal from a plurality of sensors for defining a respective plurality of channels;

processing the input raw scalp potential signal using a plurality of pre-amplifiers thereby to provide a high input impedance, wherein each pre-amplifier includes:
(i) a wideband high impedance input and active biasing network, which presents an impedance of greater than 10 Peta-Ohms from 0.01 Hz to 400 Hz;
(ii) a high gain low noise operational amplifier, with an input impedance of 10 Tera Ohms; and (iii) a feedback network for feeding back a first feedback signal interconnected to a conductive shield surrounding the input raw scalp potential signal, and a second feedback signal for actively biasing the input raw scalp potential signal;

selecting a measurement mode configuration wherein the measurement mode configuration is selected from the group consisting of:

a channel to reference-channel mode;

a channel to channel-average mode; and a channel to channel differential mode;

biasing said processed input signal while maintaining high input impedance;

matching channel gain before differentially deriving a channel signal for each of the plurality of channels;

processing each channel signal using the selected measurement mode configuration thereby to provide a corresponding processed channel signal, wherein the processing of each channel signal includes:

suppressing radio frequency interference of each channel signal while maintaining gain and phase matching; and suppressing common mode signal interference of each channel signal;

band pass filtering each said processed channel signal; and digitizing each said processed channel signal thereby to provide a digital scalp potential measurement signal indicative of said scalp potential signals having been processed.

2. A method according to claim 1 wherein each pre-amplifier includes a high input impedance amplifier for amplifying said raw scalp potential signal, and wherein the method includes amplifying said raw scalp potential signal to produce a pre-amplified scalp potential measurement.

3. A method according to claim 2 wherein said input impedance provided by each pre-amplifier is higher with respect to the impedance associated with a source interface presented to each said sensor.

4. A method according to claim 3 wherein said source interface impedance is presented by at least one of a contact medium, scalp, and underlying tissues.

5. A method according to claim 2, wherein said input impedance provided by each pre-amplifier is active and increased by the application of feedback.

6. A method according to claim 1, wherein said high gain low noise operational amplifier is a rail-to-rail FET input operational amplifier.

7. An apparatus for processing scalp potential signals comprising:

a plurality of sensors for receiving an input raw scalp potential signal, wherein the plurality of sensors define a respective plurality of channels;

a plurality of pre-amplifier modules each including a pre-amplifier for processing the input raw scalp potential signal thereby to provide a high input impedance, wherein each pre-amplifier includes:

(ii) a wideband high impedance input and active biasing network, which presents an impedance of greater than 10 Peta-Ohms from 0.01 Hz to 400 Hz;

(iii) a high gain low noise operational amplifier, with an input impedance of 10 Tera Ohms; and (iv) a feedback network for feeding back a first feedback signal interconnected to a conductive shield surrounding the input raw scalp potential signal, and for actively biasing the input raw scalp potential signal;

a channel interconnection module adapted to select a measurement mode from the group consisting of:

a channel to reference-channel mode;

a channel to channel-average mode; and a channel to channel differential mode;

an interface module for:

biasing said processed input signal while maintaining high input impedance;

matching channel gain before differentially deriving a channel signal for each of the plurality of channels;

processing each channel signal using the selected measurement mode configuration thereby to provide a corresponding processed channel signal, wherein the processing of each channel signal includes:

suppressing radio frequency interference of each channel signal while maintaining gain and phase matching; and suppressing common mode signal interference of each channel signal;

band pass filtering each said processed channel signal; and an analog-to-digital converter module for digitizing each said processed channel signal thereby to provide a digital scalp potential measurement signal indicative of said scalp potential signals having been processed.

8. An apparatus according to claim 7 wherein each pre-amplifier includes a high input impedance amplifier for amplifying said raw scalp potential signal to produce a pre-amplified scalp potential measurement.

9. An apparatus according to claim 8 wherein said input impedance provided by each pre-amplifier is higher with respect to the impedance associated with a source interface presented to each said sensor.

10. An apparatus according to claim 7, wherein said high gain low noise operational amplifier is a rail-to-rail FET input operational amplifier.

* * * * *